(12) United States Patent
Tao et al.

(10) Patent No.: US 9,488,536 B2
(45) Date of Patent: Nov. 8, 2016

(54) PROCESS FOR MANUFACTURING FABRIC PRESSURE SENSOR

(75) Inventors: Xiaoming Tao, Hong Kong (CN); Tao Hua, Hong Kong (CN); Yangyong Wang, Hong Kong (CN); Qiao Li, Hong Kong (CN); Yee Kwan Chow, Hong Kong (CN)

(73) Assignee: THE HONG KONG RESEARCH INSTITUTE OF TEXTILES AND APPAREL LIMITED, Hung Hom, Kowloon (HK)

( * ) Notice: Subject to any disclaimer, the term of this patent is extended or adjusted under 35 U.S.C. 154(b) by 373 days.

(21) Appl. No.: 13/825,124

(22) PCT Filed: Aug. 23, 2011

(86) PCT No.: PCT/CN2011/078742
§ 371 (c)(1),
(2), (4) Date: May 31, 2013

(87) PCT Pub. No.: WO2012/037843
PCT Pub. Date: Mar. 29, 2012

(65) Prior Publication Data
US 2013/0269172 A1    Oct. 17, 2013

(30) Foreign Application Priority Data
Sep. 20, 2010 (CN) .......................... 2010 1 0287822

(51) Int. Cl.
*G01L 1/00* (2006.01)
*G01N 27/04* (2006.01)
(Continued)

(52) U.S. Cl.
CPC . *G01L 1/00* (2013.01); *G01L 1/20* (2013.01); *G01L 1/205* (2013.01);
(Continued)

(58) Field of Classification Search
CPC H04R 31/00; H04R 31/006; H04R 2231/00; G01L 1/00; G01L 1/20; G01L 1/205; G01L 11/025; Y10T 29/53; Y10T 29/49004; Y10T 29/49117
See application file for complete search history.

(56) References Cited

U.S. PATENT DOCUMENTS

| 8,191,433 B2 | 6/2012 | Tao et al. |
| 2007/0202765 A1 | 8/2007 | Krans et al. |
| 2009/0272197 A1 | 11/2009 | Ridao Granado et al. |

FOREIGN PATENT DOCUMENTS

| CN | 1884987 A | 12/2006 |
| CN | 1985761 A | 6/2007 |

(Continued)

*Primary Examiner* — Carl Arbes
(74) *Attorney, Agent, or Firm* — Ella Cheong Hong Kong; Sam T. Yip (57) ABSTRACT

A process for manufacturing a fabric pressure sensor comprises cutting a sensing fabric to a pre-determined size, connecting a flexible electric wire with a wire of the sensing fabric by sewing, fixing the sensing fabric by means of a clamping positioner at a pre-determined tension, bonding a lower conversion layer with the sensing fabric by means of a lower conversion layer positioning box, bonding an adjustable column with the sensing fabric by means of an upper conversion layer positioning box, and bonding the upper conversion layer with the adjustable column by means of the upper conversion layer positioning box. A tool for manufacturing the sensor comprises an electrical property measuring device, a wire connecting tool, and a sensor structural component assembling tool. The present invention provides an easy and convenient way of manufacturing a fabric pressure sensor, monitoring the quality of manufacture, and enhancing the manufacturing precision and product yield.

5 Claims, 7 Drawing Sheets

(51) Int. Cl.
    *G01L 1/20*     (2006.01)
    *G01L 11/02*     (2006.01)

(52) U.S. Cl.
    CPC .................. *G01L 11/025* (2013.01); *G01N 27/04* (2013.01); *Y10T 29/49004* (2015.01); *Y10T 29/49117* (2015.01); *Y10T 29/53* (2015.01)

(56) References Cited

FOREIGN PATENT DOCUMENTS

| | | | |
|---|---|---|---|
| CN | 101393058 A | | 3/2009 |
| GB | 1 410 967 | * | 10/1975 |
| JP | 0659488 U | * | 8/1994 |

* cited by examiner

PROCESS FOR MANUFACTURING FABRIC PRESSURE SENSOR

CROSS-REFERENCE TO RELATED APPLICATIONS

The present application is a United States national phase application of PCT/CN2011/078742 filed Aug. 23, 2011, which claims benefit from a Chinese patent application number 201010287822.4 filed Sep. 20, 2010, and the disclosure of which is incorporated herein by reference and its entirety.

TECHNICAL FIELD

The present invention relates to manufacturing of a sensor, more particularly, to a process and tool for manufacturing a fabric pressure sensor.

BACKGROUND ART

Pressure sensors have a wide range of applications for industrial and personal use, but most pressure sensors are not suitable for the users to wear due to drawbacks such as large in size, high weight, hard touch feeling and inconvenience to use. Thus, their applications for personal use are highly limited, for example, sports clothing, smart clothing, footwear, etc, which are on the occasion in close contact with human body for pressure measurement. Fabric pressure sensor is a new type of pressure sensor. As it is mainly composed of resistance-type fabric sensing element and flexible structural material, it has many advantages, such as soft touch, light weight, long life span, and suitability for three-dimensional and large-area measurement. Fabric pressure sensor and its products have a wide range of applications in clothing and footwear, health care and rehabilitation, clinical medicine, sports, safety and protection, automobiles, aerospace, construction and other fields.

Figure 1:
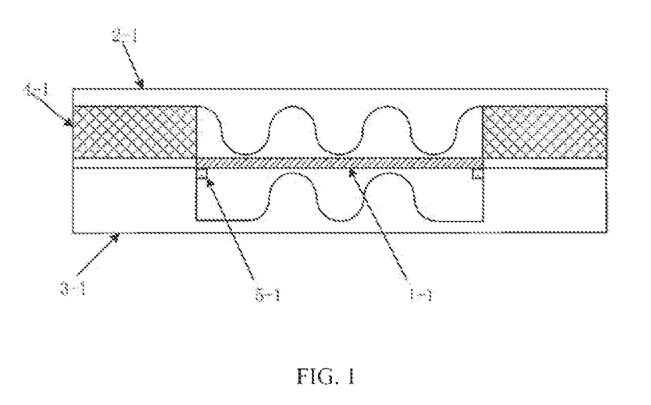
FIG. 1 is a schematic diagram showing the structure of one embodiment of the fabric pressure sensor.
Figure 2:
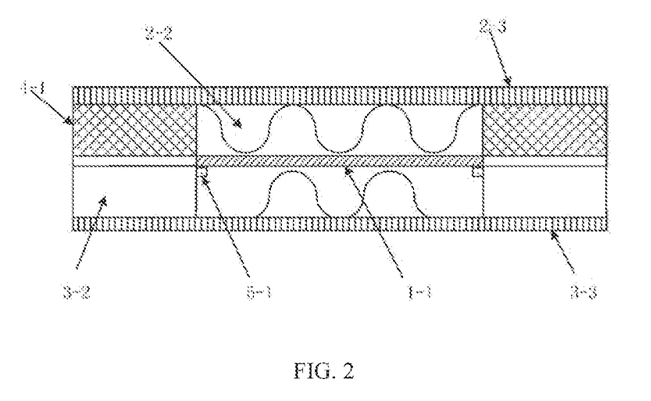
FIG. 2 is a schematic diagram showing the structure of another embodiment of the fabric pressure sensor.

FIG. 1 and FIG. 2 show the schematic views of two fabric pressure sensors respectively. The fabric pressure sensor adopts a sandwich structure, which comprises a resistance-type fabric sensing element 1-1 in the middle, an upper conversion layer based on silicone 2-1 or silicone-fabric composite (silicone 2-2, fabric 2-3) on the top, a lower conversion layer based on silicone 3-1 or silicone-fabric composite (silicone 3-2, fabric 3-3) at the bottom, an adjustment column 4-1 and a connecting wire 5-1 of the sensing fabric. The external pressure exerted on the upper and lower conversion layers convert into the deformation of the sensing fabric in the middle, thereby causing the change in resistance of the sensing fabric and output. The contour in the middle of the upper and lower conversion layers may adopt the toothed shape as shown in the figures or other shapes according to the application requirements. The stiffness of the material used for the adjustment column 4-1 can be adjusted to adapt to the different measurement requirements. The fabric pressure sensor in FIG. 1 uses silicone-based upper and lower conversion layers, and the fabric pressure sensor in FIG. 2 uses the conversion layers based on silicone-fabric composite.

Different from conventional silicone-based and film-type pressure sensors, the fabric pressure sensors are made of flexible materials, which deform easily in the manufacturing process. Therefore, it is necessary to develop and establish a corresponding process, equipment and tool for manufacturing flexible pressure sensors.

SUMMARY OF THE INVENTION

In respect of the technical problems which include the difficulties in manufacturing fabric pressure sensors using the conventional technologies and lack of the corresponding manufacturing tools, the present invention provides a process and the corresponding tools for manufacturing the fabric pressure sensors which enable simple manufacturing and control over the processing quality and product yield.

The technical solutions conferred by the present invention to solve the above-mentioned technical problems is a process for manufacturing fabric pressure sensors which comprises the following steps:

S1. Cut a sensing fabric to a pre-determined size, and connect a flexible electric wire with a wire of said sensing fabric by sewing;

S2. Fix said sensing fabric by a clamping positioner at a predetermined tension;

S3. Bond a lower conversion layer with said sensing fabric by a lower conversion layer positioning box;

S4. Bond an adjustment column with said sensing fabric by an upper conversion layer positioning box, and bond the upper conversion layer with said adjustable column by the upper conversion layer positioning box.

In the process for manufacturing a fabric pressure sensor according to the present invention, the following steps are included between step S1 and step S2:

S11. Use an electrical property measuring device to measure the conductivity and sensitivity of said sensing fabric;

S12. Use a wire connecting tool to connect said sensing fabric with a wire;

S13. Use a resistance meter to determine the quality of the connection between said sensing fabric and said wire according to the conductivity and the sensitivity of said sensing fabric.

In the process for manufacturing a fabric pressure sensor according to the present invention, the following steps are additionally included after step S4:

S5. Apply pressure to the bonding areas among the lower conversion layer, the sensing fabric, the adjustable column and the upper conversion layer through a positioning bonding weight plate.

The present invention also provides an electrical property measuring device for measuring the electrical properties of the sensing fabric, which comprises adjustable test electrodes (11) configured to contact with both ends of said sensing fabric, a resistance meter (12) for reading the resistance value of said sensing fabric, a sample station (13), and a clamper (17) for fixing said sensing fabric on the sample station and applying a pulling force and predetermined strain to both ends of said sensing fabric.

The electrical property measuring device according to the present invention further comprises an adjustment block (14) for applying pressure to said test electrodes (11), and said pressure is used to change the contact between said test electrodes (11) and said sensing fabric.

The present invention also provides a wire connecting tool for connecting the sensing fabric with a wire, and said wire connecting tool includes a wire distance control hole (21) located in the middle of said wire connecting tool, and a fixed platform (22) for fixing said sensing fabric and connecting said sensing fabric with said wire through sewing.

In the wire connecting tool according to the present invention, the surface of said fixed platform (22) also includes a wire indicating line (23) for indicating the position of said wire.

The present invention also provides a sensor structural component assembling tool for assembling the fabric pressure sensor, and said sensor structural component assembling tool comprises a clamping positioner (31) for fixing said sensing fabric at a pre-determined tension, a lower conversion layer positioning box (32) for bonding a lower conversion layer with said sensing fabric, and an upper conversion layer positioning box (33) for bonding an adjustment column with said sensing fabric and bonding an upper conversion layer with said adjustment column.

The sensor structural component assembling tool according to the present invention further comprises a positioning bonding weight plate (34) which applies pressure to the bonding area among said lower conversion layer, said sensing fabric, said adjustment column and said upper conversion layer.

In the sensor structural component assembling tool according to the present invention, the said positioning bonding weight plate (34) includes a plurality of raised heads (341) for applying pressure to the selected bonding area.

The process for manufacturing a fabric pressure sensor according to the present invention has the following advantages: it is not only an easier and more convenient process in manufacturing of the fabric pressure sensor but is also capable of monitoring the manufacturing quality, and enhancing the manufacturing precision and product yield of the flexible fabric pressure sensor.

Prior to the manufacture, the conductivity and sensitivity of the sensing fabric can be measured in order to better control the quality of the pressure sensor while suitable sensing fabric can be selected according to application requirements of the pressure sensor. The electrical property measuring device is used to quantify the relationship between resistance and tensile strain of the sensing fabrics in different lengths. The adjustment block is used to quantify the relationship between strain and resistance of the sensing fabric under different contact pressures, so as to calculate the sensitivity of the sensing fabric. The wire connecting tool is capable of well controlling the distance between two ends of the sensing fabric under testing and ensuring that the distance between the two ends of the sensing fabric under testing is consistent. The wire indicating line improves the parallelism and spacing accuracy of the wires in the connection process, thus ensuring the connection quality and consistency. The sensor structural component assembling tool ensures that the sensing fabric is fixed and placed in the pressure sensor in a specified position and at a pre-determined tension, so that the layers of the fabric pressure sensor can be well connected and accurately positioned. A plurality of raised heads enables accurate positioning of the bonding area, and applies the pressure for positioning. The positioning bonding weight plate ensures that the connection between the upper conversion layer, the sensing fabric and the lower conversion layer is firmer to avoid dislocation movement.

BRIEF DESCRIPTION OF THE DRAWINGS

Below is a further illustration of the present invention by using a combination of figures and embodiments. Brief description of the figures is as follows.

DETAILED DESCRIPTION OF THE INVENTION

To better illustrate the purpose, technical solutions and advantages of the present invention, the present invention is further described below with an aid of both figures and examples together. It should be understood that the examples described hereinafter are only for the purpose of illustrating the present invention, but not for limiting the scope of the present invention.

Figure 3:
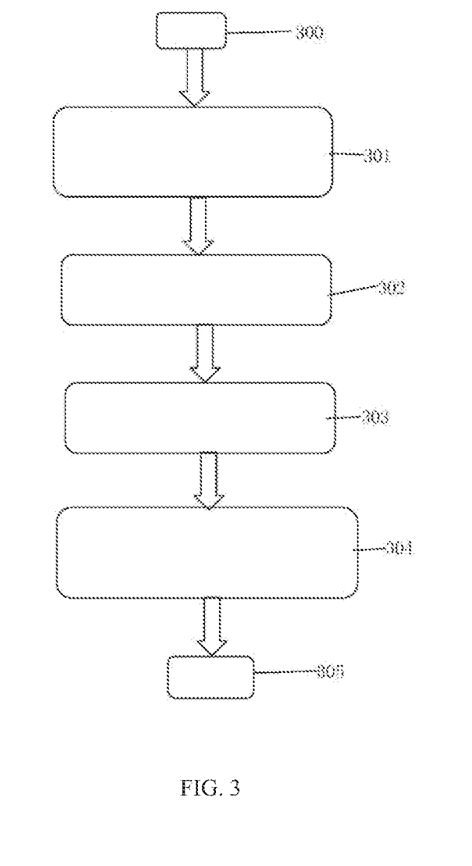
FIG. 3 is a flow diagram of the process for manufacturing a fabric pressure sensor according to a first embodiment of the present invention.

As shown in FIG. 3, that is, the flow diagram of the process for manufacturing a fabric pressure sensor according to a first embodiment of the present invention, the process starts from step 300 which provides an unmodified sensing fabric followed by step 301 which cuts the unmodified sensing fabric to a pre-determined size, and subsequently connects a flexible electric wire with a wire of said sensing fabric by sewing. In a subsequent step 302, a clamping positioner is used to fix said sensing fabric at a pre-determined tension. Following 302 is step 303 which bonds a lower conversion layer with said sensing fabric by a lower conversion layer positioning box. It is then followed by step 304 which bonds an adjustment column with said sensing fabric by an upper conversion layer positioning box, and also bonds the upper conversion layer with said adjustment column by the upper conversion layer positioning box. Finally, step 305 results in the fabric pressure sensor manufactured by the process as described in this embodiment. Using the process according to the present invention makes the manufacture of the fabric pressure sensor more easily and conveniently than any of the conventional methods.

Figure 4:
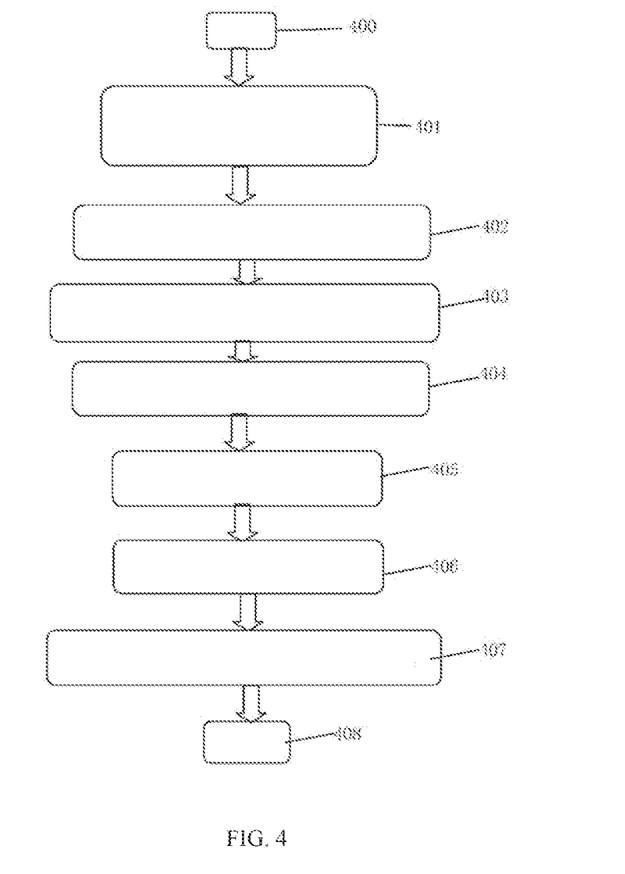
FIG. 4 is a flow diagram of the process for manufacturing a fabric pressure sensor according to a second embodiment of the present invention.

As shown in FIG. 4, that is, the flow diagram of the process for manufacturing a fabric pressure sensor according to a second embodiment of the present invention, the process starts from step 400 which provides an unmodified sensing fabric, followed by step 401 which cuts the unmodified sensing fabric to a pre-determined size, and subsequently connects a flexible electric wire with a wire of said sensing fabric by sewing. In a subsequent step 402, an electrical property measuring device is used to measure the conductivity and sensitivity of said sensing fabric. Following 402 is step 403 where a wire connecting tool and the sewing method are employed to connect said sensing fabric with a wire. It is then followed by step 404 where a resistance meter is used to determine the quality of connection between said sensing fabric and said another wire according to the conductivity and the sensitivity of said sensing fabric. In a subsequent step 405, a clamping positioner is used to fix said sensing fabric at a pre-determined tension. Following 405 is step 406 which bonds a lower conversion layer with said sensing fabric by a lower conversion layer positioning box. The subsequent step 407 bonds an adjustment column with said sensing fabric by an upper conversion layer positioning box, and also bonds the upper conversion layer with said adjustment column by the upper conversion layer positioning box. Finally, step 408 results in the fabric pressure sensor manufactured by the process as described in this embodiment. Using the process for manufacturing a fabric pressure sensor according to the present invention makes the manufacture of the fabric pressure sensor more easily and conveniently than any of the conventional methods. Prior to the manufacture, the measurement of the conductivity and sensitivity of the sensing fabric enables better connection among the sensing fabric, the upper conversion layer and the lower conversion layer, and an excellent contact with the wire.

Figure 5:
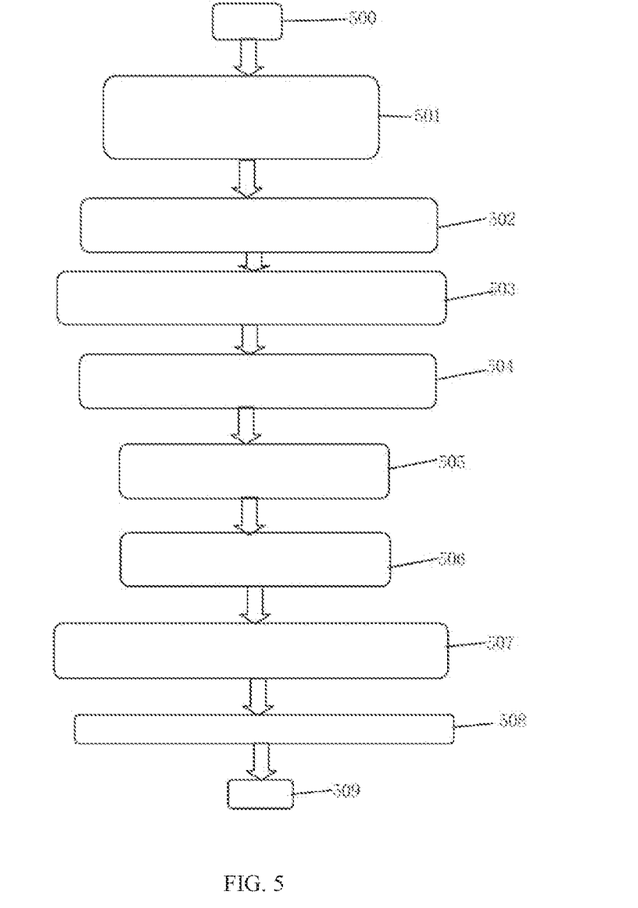
FIG. 5 is a flow diagram of the process for manufacturing a fabric pressure sensor according to a third embodiment of the present invention.

As shown in FIG. 5, that is, the flow diagram of the process for manufacturing a fabric pressure sensor according to a third embodiment of the invention, the process starts from step 500 which provides an unmodified sensing fabric, followed by step 501 which cuts the unmodified sensing fabric to a pre-determined size, and subsequently connects a flexible electric wire with a wire of said sensing fabric by sewing. In a subsequent step 502, an electrical property measuring device is used to measure the conductivity and sensitivity of said sensing fabric. Following 502 is step 503 where a wire connecting tool and the sewing method are employed to connect said sensing fabric with a wire. It is then followed by step 504 where a resistance meter is used to determine the quality of connection between said sensing fabric and said another wire according to the conductivity and the sensitivity of said sensing fabric. In a subsequent step 505, a clamping positioner is used to fix said sensing fabric at a pre-determined tension. Following 505 is step 506 which bonds a lower conversion layer with said sensing fabric by a lower conversion layer positioning box. The subsequent step 507 bonds an adjustment column with said sensing fabric by an upper conversion layer positioning box, and bond the upper conversion layer with said adjustment column by the upper conversion layer positioning box. It is followed by step 508 which applies a pressure to the bonding area through a positioning bonding weight plate. Finally, step 509 results in the fabric pressure sensor manufactured by the process described in this embodiment. Applying said pressure to the bonding area through the positioning bonding weight plate ensures that the connection between the upper conversion layer, the sensing fabric and the lower conversion layer be firmer to avoid dislocation movement.

Figure 6:
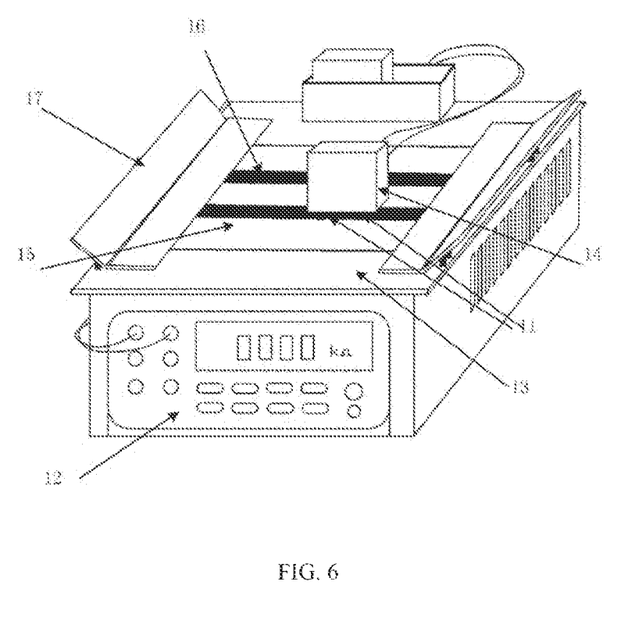
FIG. 6 is a schematic diagram showing the structure of the electrical property measuring device according to an exemplary embodiment of the present invention.

As shown in FIG. 6, that is, the schematic diagram showing the structure of the electrical property measuring device according to an exemplary embodiment of the present invention. The device comprises a resistance meter 12, a sample station 13 and test electrodes 11. The test electrodes 11 are used to contact both ends of said sensing fabric; the resistance meter 12 is used to read the resistance value of said sensing fabric; and the sample station 13 is used to fix said sensing fabric and apply pulling force to both ends of said sensing fabric. During testing, a resistance-type sensing fabric sample 15 to be tested is placed on the sample station and kept flat throughout the entire process, followed by applying a pulling force to both ends of the sensing fabric to reach the pre-determined strain of the fabric which the value of the strain can be read from the measuring scale of the sample station 13. By adjusting the pulling force at both ends of the sensing fabric, the strain applied on the sensing fabric can be adjusted. Subsequently, clamps 17 located at both sides of the sample station are used to clamp and fix the sensing fabric. The test electrodes 11 are placed on the conducting layer 16 of the sensing fabric to test the resistance of the sensing fabric. The spacing of the test electrodes 11 can be adjusted to test the resistance of the samples in different lengths. Through adjusting the adjustment block 14 which is used to apply pressure on the top of the test electrodes 11, the contact pressure between the test electrodes 11 and the conducting layer 16 of the sensing fabric can be adjusted. The resistance of the sensing fabric is read from the resistance meter 12. According to the rate of the change in resistance and strain of the fabric sample 15, the sensitivity coefficient of the sensing fabric can also be calculated by the following formula:

$$K=(\Delta R/R0)/\epsilon \qquad (1)$$

where K is the sensitivity coefficient of the sensing fabric, R0 is the initial resistance of the sensing fabric, $\Delta R$ is the resistance change amount of the sensing fabric, and $\epsilon$ is the strain applied to the sensing fabric. The electrical property measuring device can quantify the relationship between resistance and tension strain for the sensing fabrics of different lengths; the presence of adjustment block 14 can allow quantifying the relationship between strain and resistance of the sensing fabric under different contact pressures, so as to calculate the sensitivity of the sensing fabric.

Figure 7:
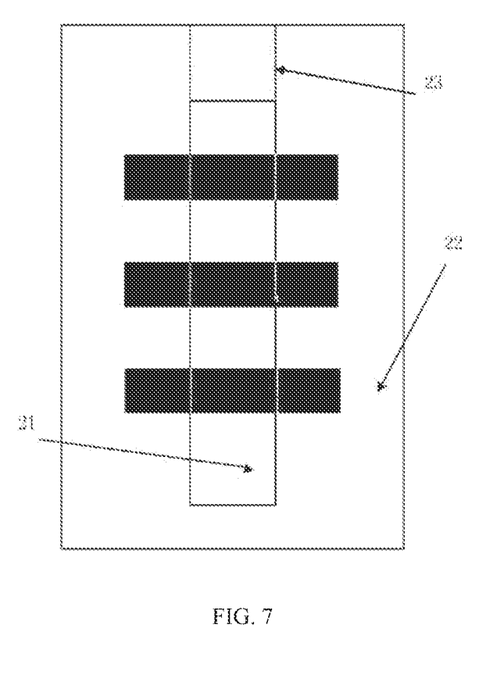
FIG. 7 is a schematic diagram showing the structure of the wire connecting tool according to an exemplary embodiment of the present invention.

As shown in FIG. 7, that is, the schematic diagram showing the structure of the wire connecting tool of an exemplary embodiment of the present invention. The wire connecting tool comprises a wire distance control hole 21, a fixed platform 22 and a wire indicating line 23. The wire distance control hole 21 is located in the middle of said wire connecting tool which is used to control the spacing of a wire; the fixed platform 22 is used to fix the sensing fabric and connect the sensing fabric with the wire through sewing; and the wire indicating line 23 is situated on the surface of the fixed platform 22 which is used to indicate the position of the wire. During wire connection, the sensing fabric is firstly placed on the fixed platform 22 at a certain pre-determined tension and kept flat throughout the entire process. Secondly, both ends of the sensing fabric are fixed on the fixed platform 22 across the wire distance control hole 21 so that the sensing fabric is not easy to be deformed during the connection thereof with the wire through sewing and the consistency of the connection can be well maintained. The wire indicating line 23 is used to hold the fabric conducting strip perpendicular to the wire when the sensing fabric is being placed on the fixed platform, and to determine the connection position of the wire on the sensing fabric. The wire indicating line 23 can also improve the parallelity and spacing accuracy of two wires connected with each other in the connection process, thus ensuring the connection quality and consistency. The connection between the flexible electrical wire and the wire of the sensing fabric is achieved by sewing, which ensures reliable connection and does not affect the flexibility of the sensing fabric.

Figure 8:
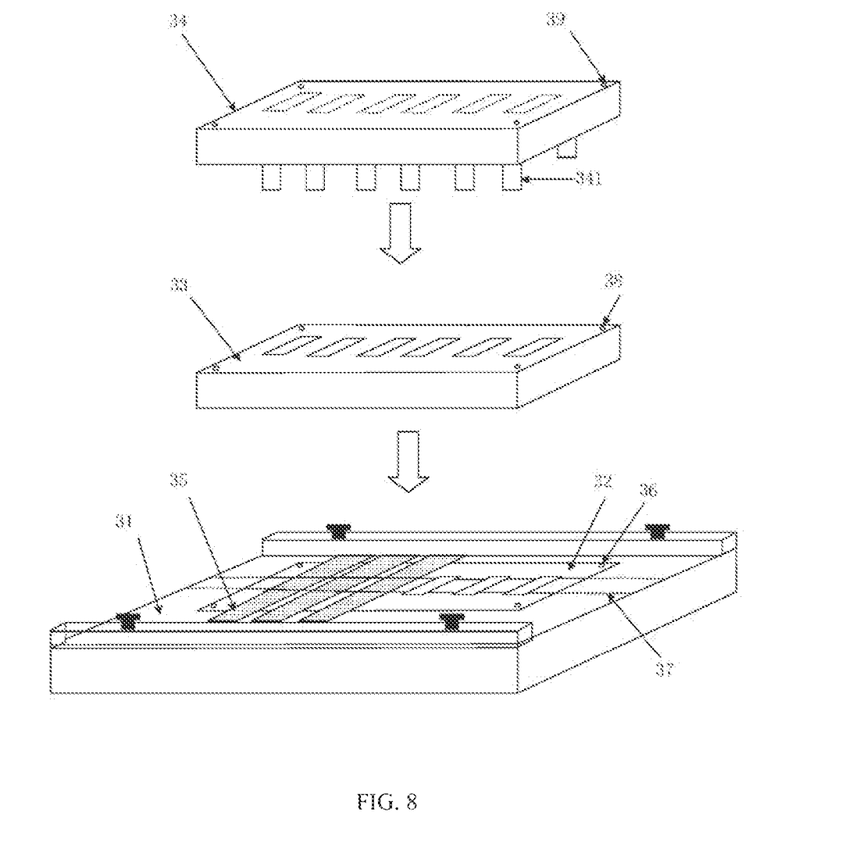
FIG. 8 is a schematic diagram showing the structure of the sensor structural component assembling tool according to an exemplary embodiment of the present invention.

As shown in FIG. 8, that is, the structural schematic diagram of the sensor structural component assembling tool of a preferred embodiment of the present invention, the sensor structural component assembling tool comprises a clamping positioner 31, a lower conversion layer positioning box 32, an upper conversion layer positioning box 33 and a positioning bonding weight plate 34. The clamping positioner 31 is used to fix said sensing fabric at a pre-determined tension; the lower conversion layer positioning box 32 is used to bond a lower conversion layer with said sensing fabric; the upper conversion layer positioning box 33 is used to bond an adjustment column with said sensing fabric, and to bond a upper conversion layer with said adjustment column; and the positioning bonding weight plate 34 is used to apply pressure to the bonding areas among said lower conversion layer, said sensing fabric, said adjustment column and said upper conversion layer, so as to ensure firm connection between them. During the assembling of the pressure sensor, the sensing fabric 35 is placed and fixed on the clamping positioner 31 in a determined position and at a pre-determined tension. Clamps situated at both sides of the clamping positioned are used to clamp two opposite sides of the sensing fabric. The connecting wire positioning slot 37 is used to position the connecting wire of the sensing fabric when the sensing fabric is placed and fixed on the clamping positioner 31. Meanwhile, the lower conversion layer is placed in the lower conversion layer positioning box 32 of the sensor structural component assembling tool, following with applying the proper amount of bonding agent to both ends of the lower conversion layer and the sensing fabric for connection. Then, the clamping positioner 31 and the lower conversion layer positioning box 32 are assembled together in a way to place the sensing fabric 35 on the lower conversion layer and ensure accurate positioning of the sensing fabric. The upper conversion layer positioning box 33 is placed on the lower conversion layer positioning box 32 and the sensing fabric 35 while the positioning of the sensing fabric should be accurate. A suitable amount of bonding agent is applied on the bonding areas of the adjustment column and upper conversion layer by placing the bonding agent according to sequence in different slots of the upper conversion layer positioning box. Then, the positioning bonding weight plate 34 is placed on the upper conversion layer positioning box followed by applying a pressure to corresponding bonding areas of the upper conversion layer, lower conversion layer, sensing fabric and the adjustment column in order for proper bonding. The positioning holes 36, 38 and 39 located on the upper conversion layer positioning box, the lower conversion layer positioning box and the positioning bonding weight plate 34 respectively are used for accurate positioning of various components of the sensor structural component assembling tool. The fabric pressure sensor of the present invention can be manufactured by the tools and process as described herein. The sensor structural component assembling tool ensures good connection between different layers of the fabric pressure sensor.

As shown in FIG. 8, according to an exemplary embodiment of the sensor structural component assembling tool of the present invention, the positioning bonding weight plate 34 includes a plurality of raised heads 341 for applying pressure to the selected bonding area. When the positioning bonding weight plate 34 is placed on the upper conversion layer positioning box, the raised heads 341 of the positioning bonding weight 34 are used to apply positioning pressure on the bonding area among the upper conversion layer, the lower conversion layer, the sensing fabric and the adjustment column for the purpose of proper bonding. The raised heads 341 enable accurate positioning of the bonding area through applying the pressure.

Below is a description of the entire manufacturing process of a fabric pressure sensor in combination with a specific embodiment.

1) Produce a resistance-type sensing fabric;

2) Test and evaluate the conductivity and sensitivity of the sensing fabric using the electrical property measuring device of the present invention;

3) Cut the sensing fabric to a pre-determined size;

4) Use the wire connecting tool of the present invention and the sewing method to connect the sensing fabric with the wires;

5) Use a resistance meter to determine the quality of connection between the sensing fabric and the wires;

6) Produce the upper conversion layer, lower conversion layer and adjustment column of the pressure sensor, and evaluate their appearance quality;

7) Place and fix the sensing fabric on the clamping positioner 31 of the sensor structural component assembling tool at a pre-determined tension;

8) Place the lower conversion layer in the lower conversion layer positioning box 32 of the sensor structural component assembling tool, and apply bonding agent to both ends of the lower conversion layer;

9) Place the clamping positioner 31 with the lower conversion layer positioning box 32 in an inlaid manner;

10) Place the upper conversion layer positioning box 33 on the lower conversion layer positioning box 32 and the sensing fabric, and apply bonding agent on the bonding area of the adjustment column and upper conversion layer, and place them in the lower conversion layer positioning box 32 in sequence;

11) Use the positioning bonding weight plate 34 to apply pressure to the bonding area among the sensing fabric, the lower conversion layer, the adjustment column and the upper conversion layer for proper bonding;

12) Finish the production of the fabric pressure sensor and evaluate its performance.

The embodiments described above are only some of the embodiments of the invention, which are not intended to limit the scope of the invention patent. Any equivalent structural transformation using the specification or its accompanying drawing of the invention, or any direct or indirect use thereof in other related technical fields shall fall within the scope of protection of the invention patent.

What is claimed is:

1. A process for manufacturing a fabric pressure sensor comprising:
   a) cutting a sensing fabric to a pre-determined size and connecting a flexible electric wire with a wire of said sensing fabric by sewing;
   b) fixing said sensing fabric by a clamping positioner at a pre-determined tension;
   c) bonding a lower conversion layer with said sensing fabric by a lower conversion layer positioning box; and
   d) bonding an adjustment column with said sensing fabric by an upper conversion layer positioning box and bonding an upper conversion layer with said adjustment column by the upper conversion layer positioning box.

2. The process for manufacturing a fabric pressure sensor according to claim 1, wherein step (a) further comprises the following steps prior to step (b):
   a1) using an electrical property measuring instrument to measure the conductivity and sensitivity of said sensing fabric;
   a2) using a wire connecting tool to connect said sensing fabric with a wire; and a3) using a resistance meter to determine the quality of connection between said sensing fabric and said wire according to the conductivity and the sensitivity of said sensing fabric.

3. The process for manufacturing a fabric pressure sensor according to claim 1, wherein step (d) further comprises:
   d1) applying a pressure to corresponding bonding areas of said lower conversion layer, sensing fabric, adjustment column and upper conversion layer through a positioning bonding weight plate.

4. The process for manufacturing a fabric pressure sensor according to claim 2, wherein said wire connecting tool comprises:
   a wire distance control hole (21) located in the middle of said wire connecting tool: and
   a fixed platform (22) for fixing said sensing fabric and connecting said sensing fabric with said wire through sewing.

5. The process for manufacturing a fabric pressure sensor according to claim 4, wherein the surface of said fixed platform (22) comprises a wire indicating line (23) for indicating the position of said wire.

\* \* \* \* \*